United States Patent
Tseng et al.

(10) Patent No.: US 6,252,227 B1
(45) Date of Patent: Jun. 26, 2001

(54) METHOD FOR SECTIONING A SEMICONDUCTOR WAFER WITH FIB FOR VIEWING WITH SEM

(75) Inventors: Fouriers Tseng; Mei Fun Chen; At Chuan Chen; Huey Ling Chen, all of Hsin-Chu (TW)

(73) Assignee: Taiwan Semiconductor Manufacturing Company, Hsin-Chu (TW)

( * ) Notice: Subject to any disclaimer, the term of this patent is extended or adjusted under 35 U.S.C. 154(b) by 0 days.

(21) Appl. No.: 09/174,653

(22) Filed: Oct. 19, 1998

(51) Int. Cl.[7] .............................. G01N 23/00; G21K 7/00
(52) U.S. Cl. ........................................... 250/307; 250/310
(58) Field of Search ............................... 250/310, 201.4; 156/643; 356/357; 438/723; 430/320

(56) References Cited

U.S. PATENT DOCUMENTS

| | | | |
|---|---|---|---|
| 4,826,564 | * 5/1989 | Desilet et al. | 156/643 |
| 4,939,364 | 7/1990 | Ishitani et al. | 250/309 |
| 4,953,982 | * 9/1990 | Ebbing et al. | 356/357 |
| 5,077,464 | * 12/1991 | Ebbing et al. | 250/201.4 |
| 5,093,572 | * 3/1992 | Hosomo | 250/310 |
| 5,212,050 | * 5/1993 | Mier et al. | 430/320 |
| 5,270,552 | 12/1993 | Ohnishi et al. | 250/307 |
| 5,525,806 | 6/1996 | Iwasaki et al. | 250/492.21 |
| 5,633,121 | 5/1997 | Namiki et al. | 430/313 |
| 6,069,092 | * 5/2000 | Imai et al. | 438/723 |

* cited by examiner

*Primary Examiner*—Jack Berman
*Assistant Examiner*—Johnnie L Smith, II
(74) *Attorney, Agent, or Firm*—George O. Saile; Stephen B. Ackerman; William Robertson

(57) ABSTRACT

An improved method for sectioning a semiconductor wafer using a focused ion beam (FIB) apparatus permits a clearer image of the site of the cut to be formed from secondary electrons produced by the beam. The clearer image helps the operator of the FIB apparatus to make a more accurate cut. Before the FIB cut is made, a laser is used to cut into the wafer to expose the lowermost layer of silicon dioxide. This oxide and any oxide splatters from the laser cut are then removed with an oxide etcher. The FIB cut can then be made without splattering silicon dioxide over the area being viewed. A low beam current is used for the FIB cut.

9 Claims, 1 Drawing Sheet

METHOD FOR SECTIONING A SEMICONDUCTOR WAFER WITH FIB FOR VIEWING WITH SEM

FIELD OF THE INVENTION

Figure 1:
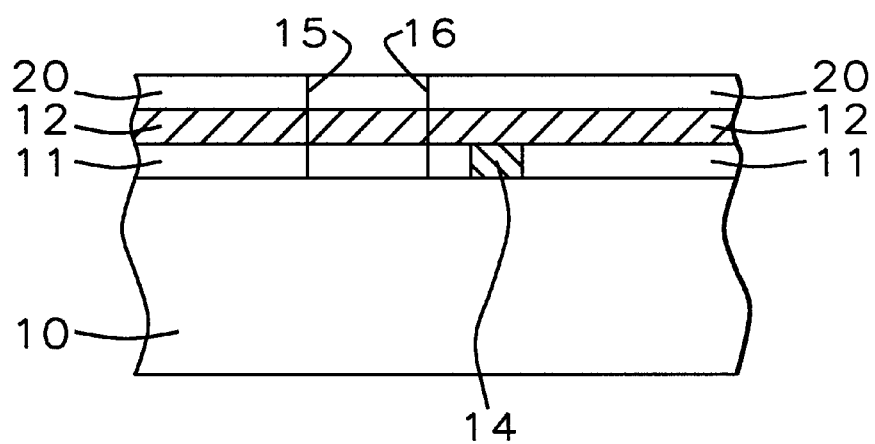

This invention relates generally to manufacturing a semiconductor wafer. More specifically, it relates to a method for preparing a semiconductor wafer for viewing with an SEM at a selected site on the wafer

INTRODUCTION

A semiconductor wafer is often tested by sectioning the wafer and then observing the section with a scanning electron microscope (SEM). The SEM produces a beam of electrons that is focused on a point in the section, and electrons that are reflected from the point are detected by an electron detector.

The electrons reflect differently from different materials, primarily according to whether a material is a conductor or non-conductor, and in this way the electrons provide an image of the point where they strike the section. The electron beam is scanned across the section in a way that is analogous scanning by a television camera, and a cathode ray tube (CRT) displays the detector signal in synchronism with the SEM beam.

Commonly this sectioning and scanning is used to observe a test wafer after one of the steps in processing the wafer. The resulting image shows for example the layers of metal and oxide, and this information helps developers to understand the preceding steps of the semiconductor manufacturing process.

A focused ion beam apparatus (FIB) can be used for cutting the wafer section. A beam of metal ions is directed at the surface of the silicon and the beam cuts away atoms in its path. The ion beam is located normal to the surface of the wafer to form a cut with vertical walls. Secondary electrons are produced when the ions strike the silicon, and these secondary electrons are used to form an image in a way that is analogous to the way the image is produced with an SEM. The ion beam is swept across the surface of the wafer to cut a desired shape, and the secondary electrons are detected and the detector signal is displayed on a cathode ray tube. The view on the CRT guides the person making the section cut with the FIB apparatus.

Using FIB apparatus has the advantage that the section can be made as a small hole in the wafer. The SEM and FIB are combined so that the section can be viewed as soon as the section has been cut. The wafer process can then be continued and a different section can be formed to view the effect of a later process step.

THE PRIOR ART

U.S. pat. No. 5,093,572 teaches the system described in the introduction to this specification.

SUMMARY OF THE INVENTION

One object of this invention is to provide a new and improved method for sectioning a wafer that is to be viewed with an SEM. A more specific object is to improve the image formed by the FIB sectioning apparatus so that an operator is less likely to over cut the wafer beyond the line where the wafer is to be viewed.

Wafers commonly have a layer of silicon dioxide (called oxide) located directly over the substrate. Oxide is also used to fill between conducting lines or nodes to isolate these conductors.

We have found that the ion beam splatters this oxide and that deposits of the oxide are left on the wafer and interfere with the image during the step of cutting the section with the FIB apparatus.

Our new method can be summarized in four steps.

First, the wafer is capped with a layer of a passivation, preferably polysilicon or silicon nitride (Si3N4).

In a second step, a small hole is cut where the sectioning cut with the FIB apparatus is to be made later. This hole is cut from the upper surface of the wafer to the oxide overlying the substrate. This step exposes the oxide so that it can be etched away in step three. Preferably, a laser is used to make this cut.

In step three, the oxide is etched with an SiO2 etcher. This step exposes the silicon substrate underlaying the oxide.

The fourth step is the sectioning cut with FIB apparatus. During this step, the view of the operator is much clearer than in the prior art and the cut can be made more accurately. As one feature of this step, the FIB apparatus is operated with a low current.

Other advantages and features of the invention will become apparent from the drawing and the description of a preferred embodiment of our invention.

THE DRAWING

FIG. 1 is a section view of a simplified semiconductor structure that illustrates steps of our method.

THE PREFERRED EMBODIMENT—INTRODUCTION INTRODUCTION—FIG. 1

FIG. 1 shows a wafer at a place where a section is to be cut for an SEM view. The simplified wafer of the drawing has a substrate 10, a layer of oxide 11 overlying the substrate, and a layer of metal 12 formed over the oxide. Metal layer 12 forms interconnections between diffusions in the substrate and other circuit nodes, and metal conductors 14 are formed in holes in the oxide 11. Lines 15, 16 show where the cuts are made. The oxide layer 11 is removed in the region identified by lines 15, 16 in our method for preparing the wafer for SEM viewing, as will be explained. The FIB cut for the SEM view is a downward extension of lines 15, 16.

FIG. 1 is representative of a wafer having a more complex structure that may include more layers of oxide that are removed according to our invention. (The FIB cut goes all the way through the wafer.)

Step One—Forming the Cap

In the section view of FIG. 1, a polysilicon layer forms a cap 20 for our method. The cap keeps the non-oxide materials from drifting during the step of removing the oxide.

Cap 20 can also be formed of silicon nitride. Alternatively, an equivalent cap 20 of silicon nitride or metal may exist as part of the structure that is to be viewed with an SEM. In concept, a module without layer 12 could be given a cap formed of metal instead of polysilicon or silicon nitride, but forming the cap of metal is more difficult and time consuming.

Step Two—Exposing the oxide

A laser cut is made along lines 15, 16 in FIG. 1 to the uppermost layer of oxide. In the simplified wafer of FIG. 1, the laser cuts through the cap 20 and the metal layer 12. If the wafer has more than one layer of oxide at the site where the sectioning cut is being made, the laser cut is made deep enough to penetrate all of the oxide layers.

This laser cut may splatter the oxide in the general way that has been described for the cut with the FIB apparatus. However, the next step removes the splatter.

Step Three—Removing the Oxide

It is an important feature of our invention that the laser cut produces a hole through which we can remove the oxide layers by wet dips, a common technique in the manufacture of wafers.

After the oxide has been exposed by cutting away the overlying layers of the wafer, the oxide is removed. Preferably the oxide is removed with a silicon dioxide etcher. Silicon dioxide is removed by etching at various points in the manufacture of semiconductor wafers, and this step will be readily understood. Three suitable etchers are hydrogen fluoride, BOE ("buffered oxide etcher") and slope. (Slope is made with deionized water, BOE, hydrogen fluoride and ethyl alcohol in the respective amounts 129, 612, 42 and 420 ml.)

Step Four—Cutting the Section

This step is conventional except that the ion beam is less than 350 pa (pico amperes).

Without the steps of making the laser cut and removing the oxide, cutting the section might take several hours with a beam of three hundred fifty pa.

If the FIB cut is made with a current of three hundred fifty pico amperes, several hours may be required to finish the cut. With the method of this invention, the FIB cut takes about ten minutes and it is free of oxide splatter. The beam current can be reduced to about one hundred fifty pa, but a cut will take twice as long.

SUMMARY

From this description of a preferred embodiment of the invention, those skilled in the art will recognize various modifications within the spirit of the invention and the intended scope of the claims.

What is claimed is:

1. A method for preparing a semiconductor wafer for viewing with an SEM at a selected site on the wafer, the wafer having a substrate of semiconductor material, and a layer of oxide overlying the substrate that may form a residue during an operation to cut a wafer section with a focused ion beam (FIB) apparatus and thereby interfere with viewing the selected site during the operation to cut the section with the FIB apparatus, the method comprising the following steps, if the uppermost layer of the wafer is not a cap of polysilicon or silicon nitride, forming a cap of polysilicon or silicon nitride on the uppermost layer of the wafer, then, cutting a hole at the selected site through the cap and any oxide layers between the cap and the layer of oxide overlying the substrate, then, removing the oxide layer, and then using an FIB apparatus to cut the section while viewing an image of the site formed by secondary electrons from the FIB apparatus, the image being free of oxide deposits that otherwise may occur when cutting the section with the FIB apparatus.

2. The method of claim 1 where the step of cutting the hole above the oxide layer includes cutting said hole with a laser.

3. The method of claim 2 wherein the step of removing the oxide includes removing the oxide with an etcher.

4. The method of claim 3 where the step of cutting the hole above the oxide layer with a laser includes the incidental step of producing oxide splatters that interfere with viewing during a cut with an FIB apparatus.

5. The method of claim 4 wherein the step of removing the oxide includes etching the wafer to remove the oxide splatters produced by the step of cutting the hole above the oxide layer.

6. The method of claim 5 wherein the oxide etcher is BOE.

7. The method of claim 5 wherein the oxide etcher is slope.

8. The method of claim 5 wherein the oxide etcher is hydrogen fluoride.

9. The method of claim 5 wherein the step of using an FIB apparatus to cut the section includes operating the FIB apparatus at a current of less than 350 pico amperes.

\* \* \* \* \*